US008073236B2

(12) United States Patent
Peng et al.

(10) Patent No.: US 8,073,236 B2
(45) Date of Patent: Dec. 6, 2011

(54) SYSTEM AND METHOD FOR DETECTING BLEMISHES ON IMAGE SENSOR PACKAGE

(75) Inventors: Lei Peng, Foshan (CN); Jiang-Ping Wang, Foshan (CN)

(73) Assignees: Premier Image Technology (China) Ltd., Foshan, Guangdong Province (CN); Hon Hai Precision Industry Co., Ltd., Tu-Cheng, New Taipei (TW)

( * ) Notice: Subject to any disclaimer, the term of this patent is extended or adjusted under 35 U.S.C. 154(b) by 1042 days.

(21) Appl. No.: 11/946,288

(22) Filed: Nov. 28, 2007

(65) Prior Publication Data

US 2008/0317380 A1    Dec. 25, 2008

(30) Foreign Application Priority Data

Jun. 20, 2007    (CN) .......................... 2007 1 0200843

(51) Int. Cl.
  G06K 9/00    (2006.01)
  H04N 9/64    (2006.01)
  G01N 21/00    (2006.01)
(52) U.S. Cl. ...................... 382/141; 356/237.1; 348/246
(58) Field of Classification Search .......... 382/141–152; 348/246, 247; 356/237.1–237.6
  See application file for complete search history.

(56) References Cited

U.S. PATENT DOCUMENTS

| 5,717,781 | A  | * | 2/1998  | Ebel et al. ..................... 382/141 |
| 6,529,622 | B1 | * | 3/2003  | Pourjavid ..................... 382/149 |
| 7,009,644 | B1 |   | 3/2006  | Sanchez et al. |
| 7,092,018 | B1 |   | 8/2006  | Watanabe |
| 7,103,208 | B2 |   | 9/2006  | Wengender et al. |
| 7,362,916 | B2 | * | 4/2008  | Yamazaki ...................... 382/275 |
| 7,671,909 | B2 | * | 3/2010  | Uvarov et al. ................ 348/246 |
| 7,783,103 | B2 |   | 8/2010  | Kuchii et al. |
| 2002/0080917 | A1 | * | 6/2002 | Granfors et al. ............. 378/98.8 |
| 2005/0186327 | A1 | * | 8/2005 | Saito et al. ......................... 427/8 |
| 2006/0284862 | A1 | * | 12/2006 | Uvarov et al. ................ 345/204 |
| 2008/0317380 | A1 | * | 12/2008 | Peng et al. .................... 382/276 |
| 2009/0322879 | A1 | * | 12/2009 | Faber et al. ................... 348/148 |

FOREIGN PATENT DOCUMENTS

| CN | 1167035 C | 9/2004 |
| CN | 1940994 A | 4/2007 |
| TW | 479432    | 3/2002 |

* cited by examiner

Primary Examiner — Aaron W Carter
(74) Attorney, Agent, or Firm — Altis Law Group, Inc.

(57) ABSTRACT

A system for detecting blemishes on an image sensor package includes an initialization module configured for initializing a suspected blemish standard mean value range and a blemish standard deviation value; an image capturing module configured for capturing an image produced by the image sensor package and acquiring a brightness value of each of pixels of the image; a calculation module configured for calculating a mean value and a standard deviation of differences of brightness values of a pixel and any other pixels surrounding the pixel; a comparison module configured for respectively comparing the mean value and the standard deviation with the suspected blemish standard mean value range and the blemish standard deviation value; and a marking module configured for marking the suspected blemish which is inside the suspected blemish standard mean value range and the blemish which is larger than the blemish standard deviation value.

6 Claims, 6 Drawing Sheets

SYSTEM AND METHOD FOR DETECTING BLEMISHES ON IMAGE SENSOR PACKAGE

RELATED FIELD

The present invention relates to a detection technology of image sensor packages, and more particularly, to a system and a method for detecting blemishes on an image sensor package.

BACKGROUND

There are two different types of image sensor packages; charge coupled device (CCD) image sensor packages and complementary metal oxide semiconductor (CMOS) image sensor packages. An image sensor packages is basically a two dimensional array of light sensing elements, and each light sensing element is corresponding to a pixel of an image captured by the image sensor package. If these image sensor packages have blemishes that obstruct or distort light, the resulting image is of bad quality. These blemishes are classified into three different types: dust, which can be removed by cleaning; scratches, which are usually long and narrow; and pits, which are usually small and more circular in nature. When these blemishes are on the light sensing elements, undesired shadows will be cast on the light sensing elements, and thus artifacts appear in the resulting image. Scratches, pits, and dust are typically created not only during the process of handling the image sensor packages, but also during the packaging process of the image sensor packages before the image sensor packages are assembled in the final product, such as a digital camera. In the past, the detection of blemishes has been done under a microscope or by viewing an image generated on a screen. These detection techniques are subjective, time consuming, and often inaccurate.

Scratches, pits, and dust will cause corrupted data in the digital image after the digital image is read from the image sensor package. To produce the highest quality image, the scratches, pits, or dusts need to be detected during the manufacturing and assembly process so that image sensor packages of bad quality can be rejected and prevented from being assembled into the final product.

SUMMARY

In accordance with a present embodiment, a system for detecting blemishes on an image sensor package, includes an initialization module configured for initializing a suspected blemish standard mean value range and a blemish standard deviation value; an image capturing module configured for capturing an image produced by the image sensor package and acquiring a brightness value of each of pixels of the image; a calculation module configured for calculating a mean value and a standard deviation of differences of brightness values of a pixel and any other pixels surrounding the pixel; a comparison module configured for respectively comparing the mean value and the standard deviation with the suspected blemish standard mean value range and the blemish standard deviation value; and a marking module configured for marking the suspected blemish, mean value of which is inside the suspected blemish standard mean value range and the blemish, standard deviation of which is greater than the blemish standard deviation value.

Other novel features and advantages will be drawn from the following detailed description of at least one preferred embodiment, when considered in conjunction with the attached drawings.

BRIEF DESCRIPTION OF THE DRAWINGS

The present invention is described in detail hereinafter, by way of examples only and through description of preferred embodiment thereof and with reference to the accompanying drawings in which.

DETAILED DESCRIPTION OF THE PREFERRED EMBODIMENTS

A detailed explanation of a system and a method for detecting blemishes on an image sensor package according to embodiments of the present invention will now be made with reference to the drawings attached hereto.

Figure 1:
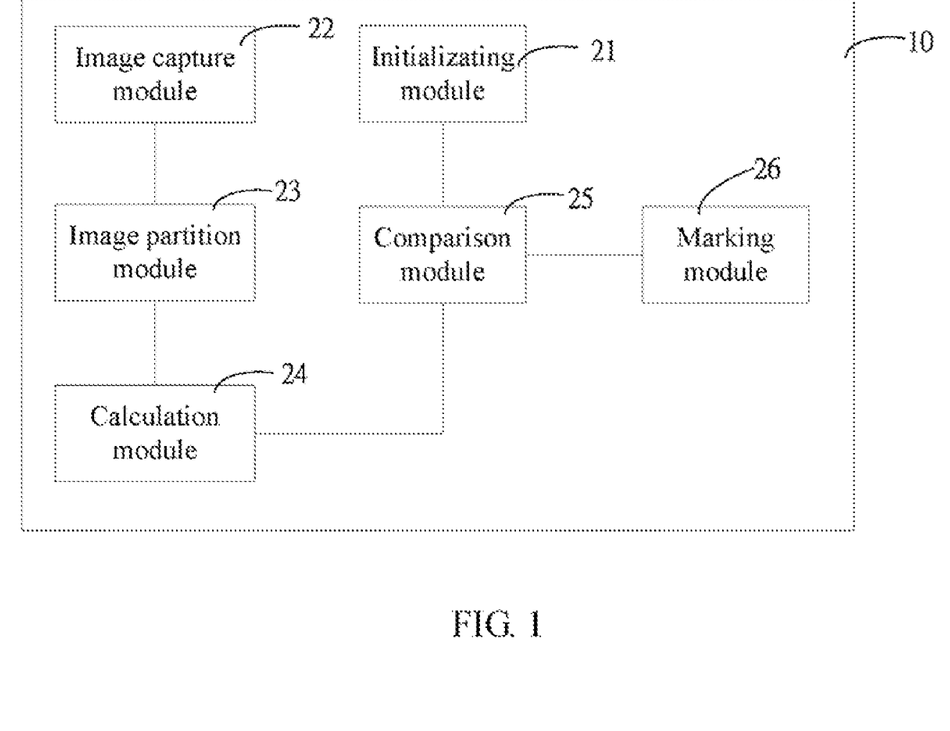
FIG. 1 is a block diagram of a system for detecting blemishes on an image sensor package according to a preferred embodiment.

Referring to FIG. 1, a block diagram of a system 10 for detecting blemishes on an image sensor package is shown. The image sensor package can be a CCD image sensor package or a CMOS image sensor package. In the present embodiment, the image sensor package is a CCD image sensor package. The system 10 is stored in a PC (not shown), and includes an image capturing module 22, an image partition module 23 electrically connected to the image capturing module 22, a calculation module 24 electrically connected to the image partition module 23, a comparison module 25 electrically connected to the image partition module 23, a marking module 26 electrically connected to the comparison module 25, and an initializing module 21 electrically connected to the comparison module 25.

Images acquired by the image capturing module 22 through the image sensor package may be contaminated by noise signals when current passes through the image sensor package to detect and record the blemishes of the images. Noise is generally generated due to radio frequency interference or overly long exposure to light and may form shadows on the captured image in much the same way as blemishes do. Therefore, noise should be distinguished from blemishes in detecting true blemishes of the image sensor package. In the present embodiment, image artifacts such as shadows are called suspected blemishes before being distinguished as being true blemishes; and the term "blemishes" is used in relation to a pixel of an image as well as the part of the image sensor package that correspond to such pixel.

The initializing module 21 is configured for initializing a suspected blemish standard mean value range and a blemish standard deviation value. The suspected blemish standard mean value range is applied to distinguish suspected blemishes from qualified pixels. The blemish standard deviation value is applied to distinguish the suspected blemishes from blemishes. The image capturing module 22 is configured for capturing an image and acquiring a brightness value of each pixel of the image. The calculation module 24 is configured for calculating a mean value and a standard deviation of differences of brightness values of a pixel and any other pixels surrounding the pixel. The comparison module 25 is configured for respectively comparing the mean value and the standard deviation with the suspected blemish standard mean value range and the blemish standard deviation value. The marking module 26 is configured for marking the suspected blemish, the mean value of which is inside the suspected blemish standard mean value range and the blemish standard deviation of which is larger than the blemish standard deviation value. The image partition module 23 is configured for partitioning the image into a number of regions. In initializing the blemish standard deviation value, the comparison module 25 compares standard deviations of a number of regions in order to acquire the blemish standard deviation. In the present embodiment, the image is partitioned into nine regions.

Figure 2:
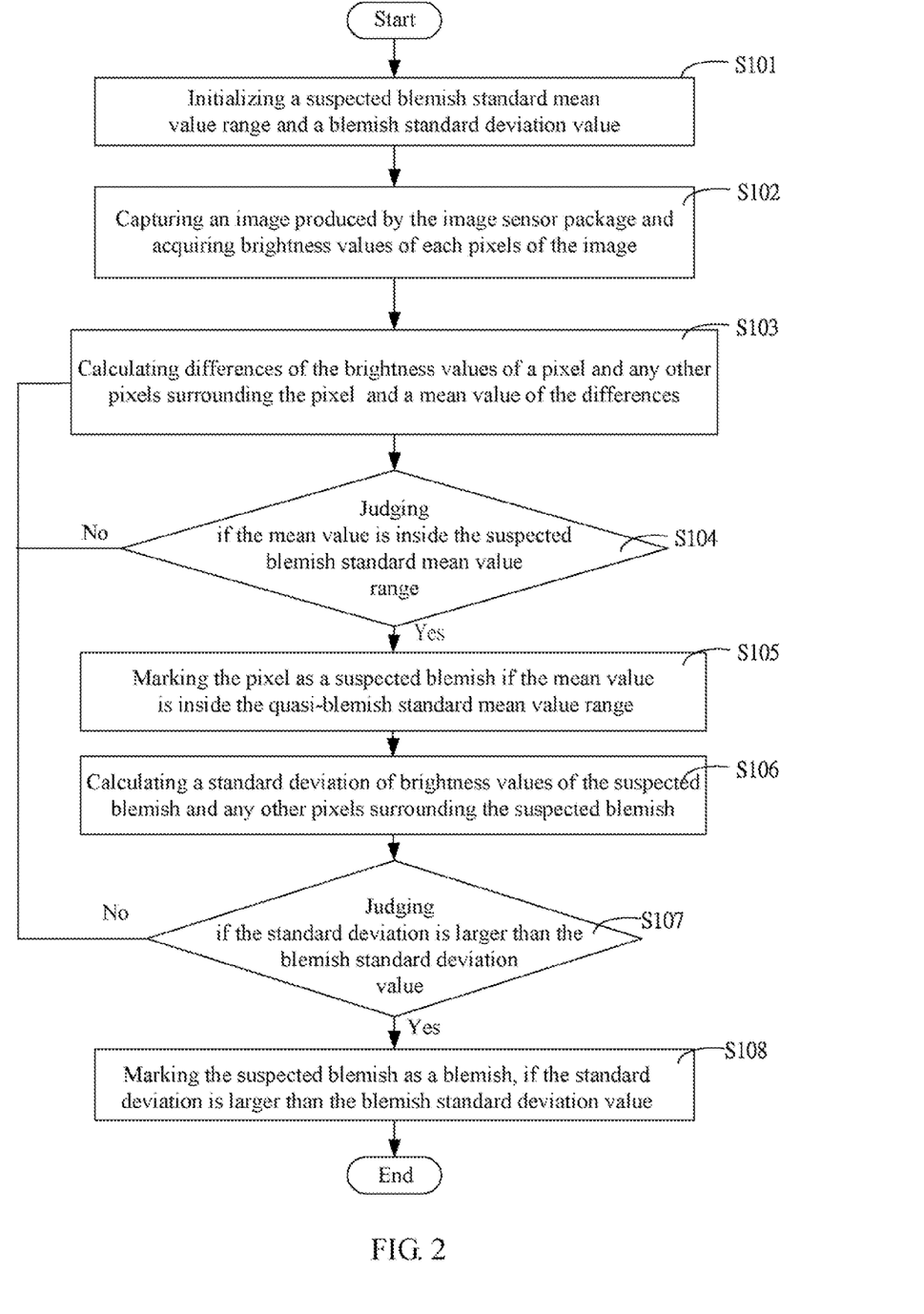
FIG. 2 is a flow chart an exemplary method for detecting blemishes on an image sensor package, utilizing the system of FIG. 1.

Referring to FIG. 2, a flow chart of an exemplary method for detecting blemishes on the image sensor package is shown. The method includes:

step S101: initializing a suspected blemish standard mean value range and a blemish standard deviation value;

step S102: capturing an image acquired through the image sensor package, and acquiring brightness values of each pixel of the image;

step S103: calculating a number of differences of the brightness values of a pixel and any other pixels surrounding the pixel and a mean value of the differences;

step S104: judging if the mean value is inside the suspected blemish standard mean value range;

step S105: marking the pixel as a suspected blemish, if the mean value is inside the suspected blemish standard mean value range;

step S106: calculating a standard deviation of brightness values of the suspected blemish and any other pixels surrounding the suspected blemish;

step S107: judging if the standard deviation is larger than the blemish standard deviation value; and step S108: marking the suspected blemish as a blemish, if the standard deviation is larger than the blemish standard deviation value.

In the method for detecting blemishes, if the detected pixel is not the last pixel in the image, the program stored in the PC continues to detect the next pixel, repeating step S103 to step S108, and so on for each remaining undetected pixel, until the last pixel is found and detected. A next process such as a cleaning process can be carried out after all the blemishes have been marked.

Figure 3:
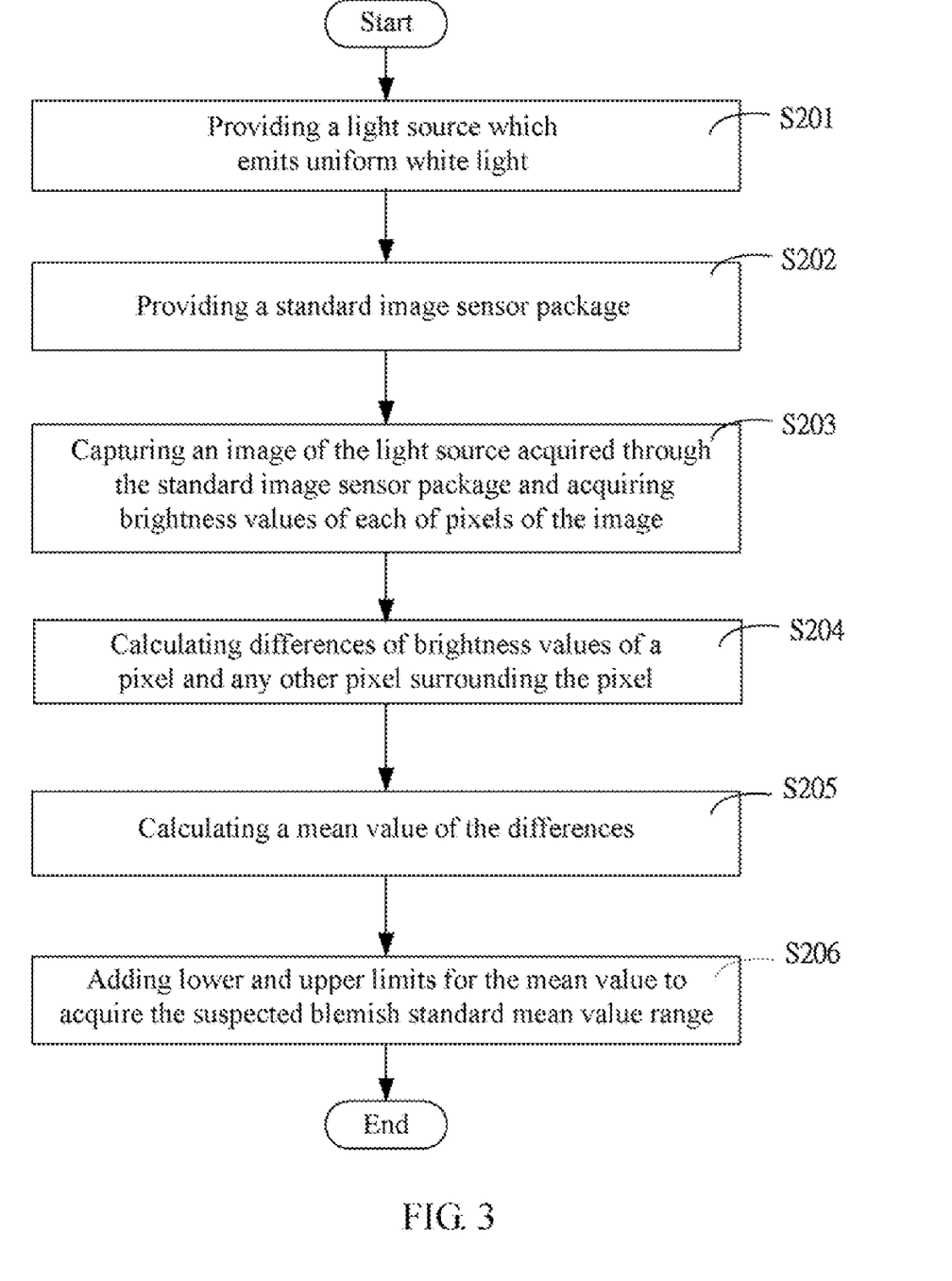
FIG. 3 is a flow chart of steps for initializing a suspected blemish standard mean value range, according to the method of FIG. 2.

In step S101, the suspected blemish standard mean value range is obtained by capturing an image via a standard (unblemished) qualified image sensor package from a light source which emits uniform white light, and calculating and comparing the mean values of brightness of each pixel of the image. Referring to FIG. 3, a flow chart of steps for initializing the suspected blemish standard mean value range includes:

step S201: providing a light source which emits uniform white light; wherein the light source can be the same as a light source used to obtained the image acquired through the image sensor package under test (see above);

step S202: providing a standard image sensor package;

step S203: capturing an image of the light source acquired through the standard image sensor package and acquiring brightness values of each of pixels of the image;

step S204: calculating differences of brightness values of a pixel and any other pixels surrounding the pixel;

step S205: calculating a mean value of the differences; and step S206: adding lower and upper limits for the mean value to acquire the suspected blemish standard mean value range.

The lower and upper limits of the suspected blemish standard mean value range are set according to demand, such as desired detecting precision. In the present embodiment, the values of the lower and upper limits are +/−3.

Figure 4:
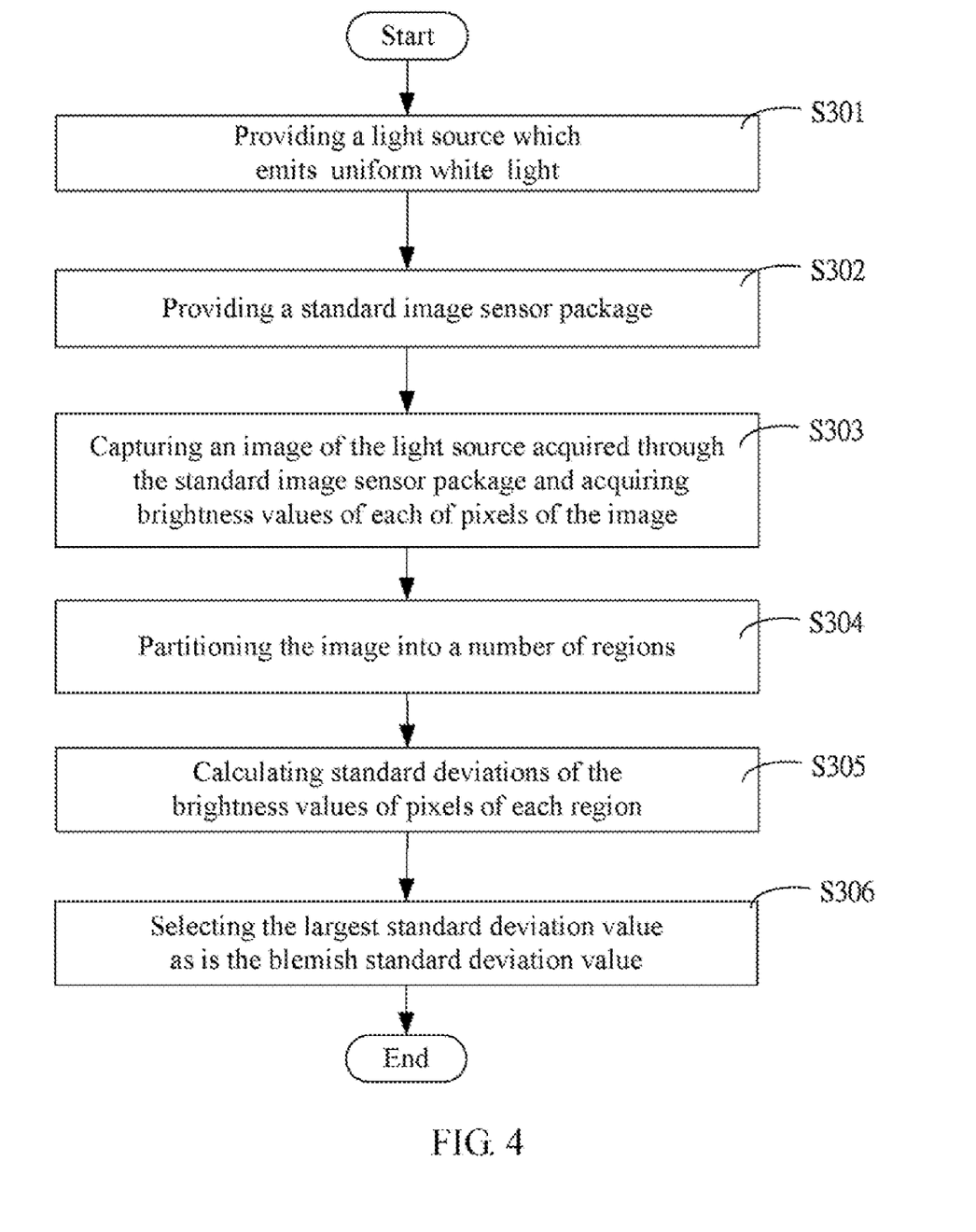
FIG. 4 is a flow chart of steps for initializing a blemish standard deviation value, according to the method of FIG. 2.

The blemish standard deviation value is obtained by capturing an image via a standard image sensor package from a light source which emits uniform white light, and analyzing the brightness values of each pixel of the image. Referring to FIG. 4, a flow chart of steps for initializing the blemish standard deviation value includes:

step S301: providing a light source which emits uniform white light;

step S302: providing a standard image sensor package;

step S303: capturing an image of the light source acquired through the standard image sensor package and acquiring brightness values of each of pixels of the image;

step S304: partitioning the image into a number of regions;

step S305: calculating standard deviations of the brightness value of pixels of each region; and step S306: selecting the largest standard deviation value as the blemish standard deviation value.

As described above, the suspected blemish standard mean value range and the blemish standard deviation value are obtained.

In step S102, the image can be captured via the image sensor package detecting a selected light source. It can be appreciated that the image is obtained through the image sensor package using a light source which emits uniform white light.

In step S103, the calculation is performed for a selected pixel.

In step S104, if the mean value of differences of the brightness values of the pixel and any other pixels surrounding the pixel is inside the suspected blemish standard mean value range, the pixel is a suspected blemish and is marked. Then step S105 is carried out. If the mean value is outside the suspected blemish standard mean value range, the pixel is a qualified pixel. Then step S103 is repeated for a next pixel if there is one.

Figure 5:
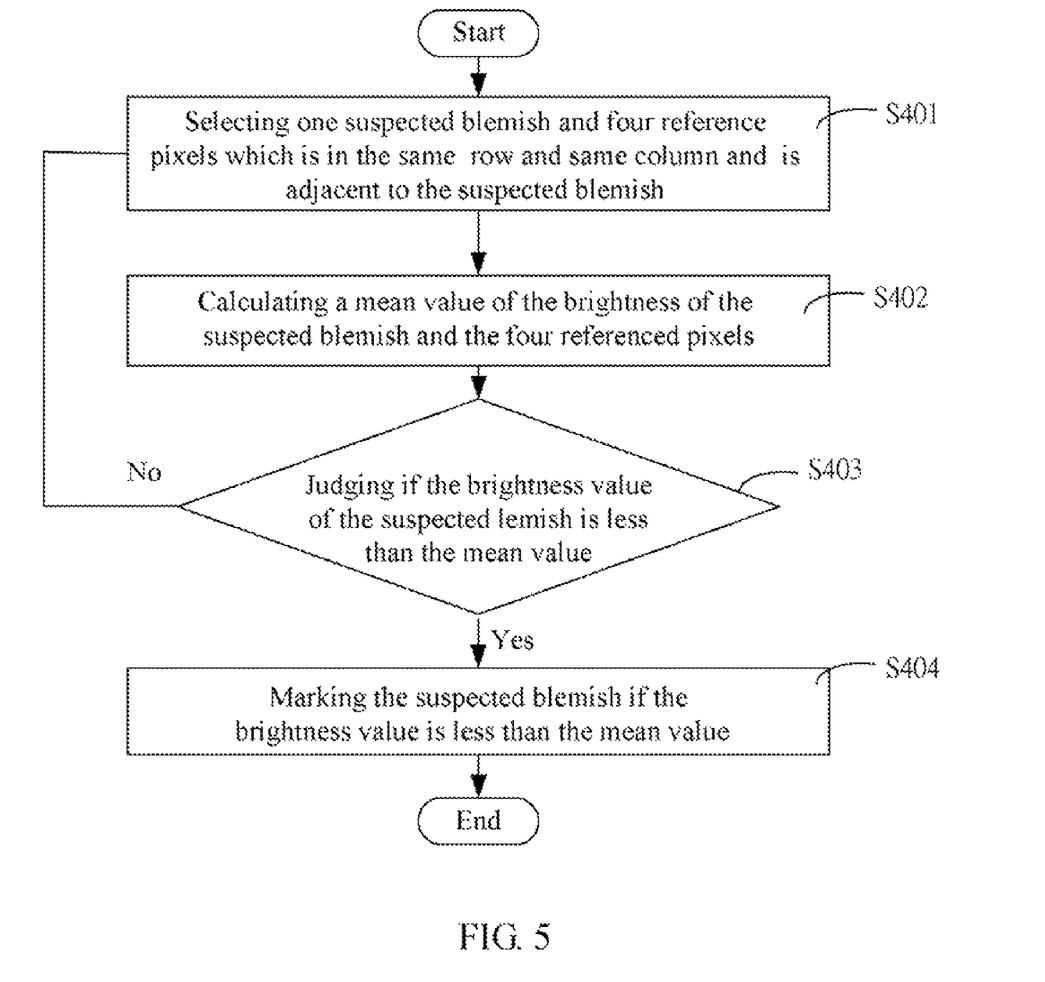
FIG. 5 is a flow chart of steps for accurately marking one suspected blemish, according to the method of FIG. 2.

In step S105, because the area of a pixel is very small, it is difficult to accurately mark the location of the suspected blemish identified in step S104. Therefore, in the present embodiment, a five-point difference locating method is applied to accurately mark the location of the suspected blemish. Referring to FIG. 5, a flow chart of steps for accurately marking the suspected blemish according to the five-point difference locating method includes:

step S401: selecting one suspected blemish and four reference pixels which are in the same row and same column and are adjacent to the suspected blemish;

step S402: calculating a mean value of the brightness of the suspected blemish and the four reference pixels;

step S403: judging if the brightness values of the suspected blemish is less than the mean value; and step S404: marking the suspected blemish if the brightness value thereof is less than the mean value.

If the brightness value of the suspected blemish is larger than the mean value, the program stored in the PC continues to detect a next suspected blemish, such as one of the four reference pixels, to confirm the location of the suspected blemish.

In step S106, the standard deviation is calculated using the following formula:

$$T=(V(X_1)+V(X_2)+\ldots+V(X_n))/n$$

$$S=(V(X_1)-T)^2+(V(X_2)-T)^2+\ldots+(V(X_n)-T)^2$$

$$S^2=\sqrt{S/n}$$

wherein:

$V(X_n)$ is a brightness value of a pixel;

T is a mean value of a number of pixels;

n is a quantity of pixels detected; and $S^2$ is the standard deviation.

Because blemishes are scratches, pits, or dust which form or drop on the image sensor package, artifacts in images cause by blemishes are typically darker than artifacts in images caused by noise, deviations in brightness values of a blemished pixel and surrounding pixels are greater than corresponding deviations in brightness values that are merely due to noise. Thus, a standard deviation of brightness values of a blemished pixel and the surrounding pixels is greater than the blemish standard deviation value, and a corresponding standard deviation of brightness values that are merely due to noise is less than the blemish standard deviation value.

Figure 6:
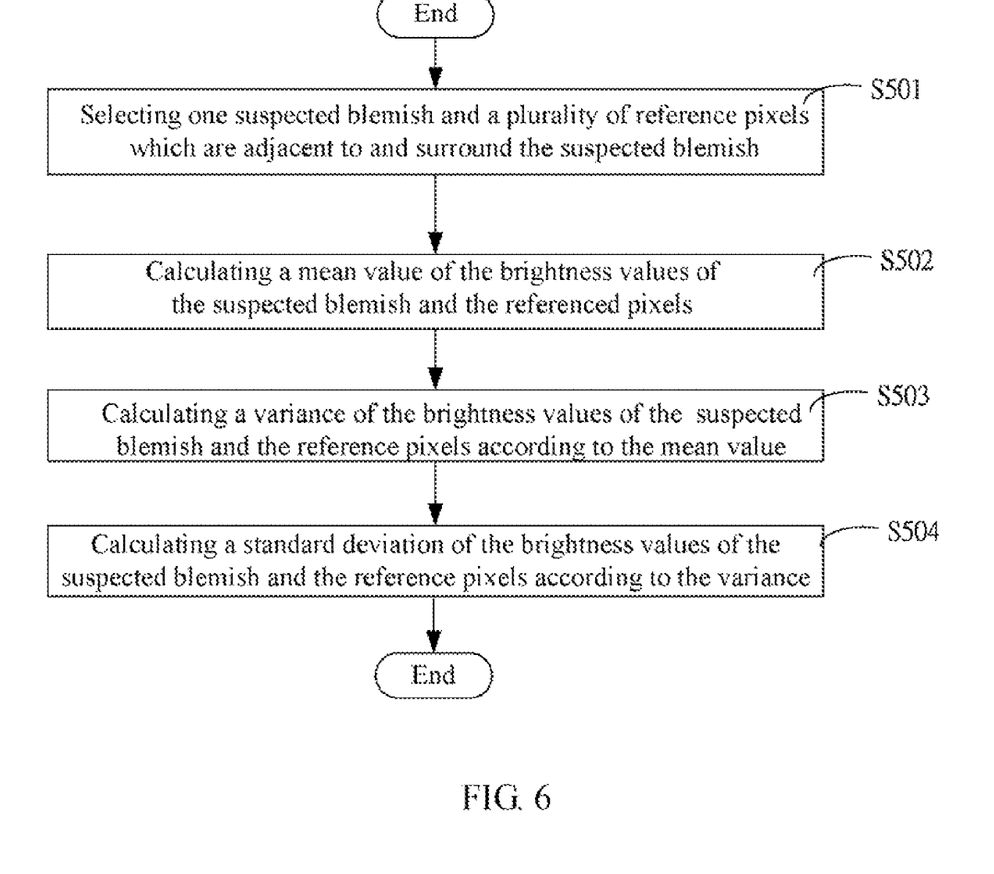
FIG. 6 is a flow chart of steps for calculating the standard deviation of a suspected blemish and any other pixels surrounding the suspected blemish, according to the method of FIG. 2.

According to mathematical principles including standard deviation, a standard deviation of brightness values of a suspected blemish can be obtained used to distinguish whether the suspected blemish is a blemish or merely a result of noise. Referring to FIG. 6, a flow chart of steps for calculating the standard deviation of brightness values of a suspected blemish and any other pixels surrounding the suspected blemish includes:

step S501: selecting one suspected blemish and a plurality of reference pixels which are adjacent to and surround the suspected blemish; wherein the quantity of reference pixels is set according to demand, such as four reference pixels which are in the same row and same column and are adjacent to the suspected blemish; further, in the present embodiment, the quantity of reference pixel is n, where n is a positive integer greater than 1;

step S502: calculating a mean value of the brightness value of the suspected blemish and the n reference pixels;

step S503: calculating a variance of the brightness values of the suspected blemish and the n reference pixels according to the mean value; and step S504: calculating a standard deviation of the brightness values of the suspected blemish and the reference pixels according to the variance.

As stated above, the standard deviation of the suspected blemish and the n reference pixels is obtained. Then the comparison of the standard deviation and the blemish standard deviation value is carried out to judge if the suspected blemish is in fact a blemish and not noise.

After the detection in steps S101 to S108 is completed, the blemishes on the image sensor package are accurately marked. Then a next process, such as cleaning the image sensor package having the blemishes, may commence.

As described above, the system and method for detecting blemishes on an image sensor package can accurately mark the location of blemishes via the five-point difference locating method and standard deviation theory. The system and method avoid errors that may otherwise occur due to the interference of noise, and avoid the subjective factors of viewers. Accordingly, the system and method can improve the efficiency of detection.

It should be understood that the above-described embodiments are intended to illustrate rather than limit the invention. Variations may be made to the embodiments including the methods without departing from the spirit of the invention. Accordingly, it is appropriate that the appended claims be construed broadly and in a manner consistent with the scope of the invention.

What is claimed is:

1. A method for detecting blemishes on an image sensor package, comprising:

initializing a suspected blemish standard mean value range and a blemish standard deviation value;

capturing an image produced by the image sensor package and acquiring brightness values of each of pixels of the image;

calculating differences of the brightness values of a selected pixel and selected other pixels surrounding the pixel and a mean value of the differences;

judging if the mean value is inside the suspected blemish standard mean value range;

marking the pixel as suspected blemish if the mean value is inside the suspected blemish standard mean value range;

calculating a standard deviation of brightness values of the suspected blemish and selected other pixels surrounding the suspected blemish;

judging if the standard deviation is larger than the blemish standard deviation value; and marking the suspected blemish as a blemish if the standard deviation is larger than the blemish standard deviation value;

wherein initializing the suspected blemish standard mean value range comprises;

providing a light source which emits uniform white light;

providing a standard image sensor package;

capturing an image of the light source produced by the standard image sensor package and acquiring brightness values of each of pixels of the image;

calculating differences of a selected pixel and selected other pixels surrounding the pixel;

calculating a mean value of the differences; and adding a lower and an upper limit for the mean value to acquire the suspected blemish standard mean value range.

2. The method as claimed in claim 1, wherein values of the lower and upper limits are +/−3.

3. The method as claimed in claim 1, wherein initializing the blemish standard deviation value comprises:

providing a light source which emits uniform white light;

providing a standard image sensor package;

capturing an image of the light source produced by the standard image sensor package and acquiring brightness values of each of pixels of the image;

partitioning the image into a plurality of regions;

calculating standard deviations of the brightness value of pixels of each region; and selecting the largest standard deviation value as the blemish standard deviation value.

4. A method for detecting blemishes on an image sensor package, comprising:

initializing a suspected blemish standard mean value range and a blemish standard deviation value;

capturing an image produced by the image sensor package and acquiring brightness values of each of pixels of the image;

calculating differences of the brightness values of a selected pixel and selected other pixels surrounding the pixel and a mean value of the differences;

judging if the mean value is inside the suspected blemish standard mean value range;

marking the pixel as suspected blemish if the mean value is inside the suspected blemish standard mean value range;

calculating a standard deviation of brightness values of the suspected blemish and selected other pixels surrounding the suspected blemish;

judging if the standard deviation is larger than the blemish standard deviation value; and marking the suspected blemish as a blemish if the standard deviation is larger than the blemish standard deviation value;

wherein marking the suspected blemish as a blemish comprises:

selecting the suspected blemish and four referenced pixels which are in the same row and same column and are adjacent to the suspected blemish;

calculating a mean value of the brightness of the suspected blemish and the four reference pixels;

judging if the brightness value of the suspected blemish is less than the mean value; and marking the suspected blemish as a blemish if the brightness value is less than the mean value.

5. The method as claimed in claim 1, wherein calculating a standard deviation of brightness values of the suspected blemish and selected other pixels surrounding the suspected blemish comprises:

selecting the suspected blemish and a plurality of reference pixels which are adjacent to and surround the suspected blemish;

calculating a mean value of the brightness values of the suspected blemish and the reference pixels;

calculating a variance of the brightness values of the suspected blemish and the referenced pixels according to the mean values; and calculating a standard deviation of the brightness values of the suspected blemish and the referenced pixels according to the variance.

6. A method for detecting blemishes on an image sensor package, comprising:

initializing a suspected blemish standard mean value range and a blemish standard deviation value;

capturing an image produced by the image sensor package and acquiring brightness values of each of pixels of the image;

calculating differences of the brightness values of a selected pixel and selected other pixels surrounding the pixel and a mean value of the differences;

judging if the mean value is inside the suspected blemish standard mean value range;

marking the pixel as suspected blemish if the mean value is inside the suspected blemish standard mean value range;

calculating a standard deviation of brightness values of the suspected blemish and selected other pixels surrounding the suspected blemish;

judging if the standard deviation is larger than the blemish standard deviation value; and marking the suspected blemish as a blemish if the standard deviation is larger than the blemish standard deviation value; wherein the standard deviation is calculated using the following formula:

$$T = (V(X_1) + V(X_2) + \ldots + V(X_n))/n$$

$$S = (V(X_1) - T)^2 + (V(X_2) - T)^2 + \ldots + (V(X_n) - T)^2$$

$$S^2 = \sqrt{S/n}$$

where: $V(X_n)$ is a brightness value of a pixel; T is a mean value of a number of pixels; n is a quantity of pixels detected; and $S^2$ is the standard deviation.

* * * * *